(12) United States Patent
Pak et al.

(10) Patent No.: US 7,144,406 B2
(45) Date of Patent: Dec. 5, 2006

(54) HAIR TRANSPLANT DEVICE

(75) Inventors: Jae Paul Pak, Torrance, CA (US);
William Richard Rassman, Los Angeles, CA (US)

(73) Assignee: New Hair Institute, Los Angeles, CA (US)

( * ) Notice: Subject to any disclaimer, the term of this patent is extended or adjusted under 35 U.S.C. 154(b) by 152 days.

(21) Appl. No.: 10/397,685

(22) Filed: Mar. 26, 2003

(65) Prior Publication Data

US 2004/0193203 A1    Sep. 30, 2004

(51) Int. Cl.
*A61B 17/34* (2006.01)
(52) U.S. Cl. ..................................................... 606/187
(58) Field of Classification Search ................ 606/187, 606/169, 170, 172, 133, 184; 604/38, 22, 604/35
See application file for complete search history.

(56) References Cited

U.S. PATENT DOCUMENTS

| 5,417,683 | A | * | 5/1995 | Shiao | ............................. 606/1 |
| 6,059,807 | A | * | 5/2000 | Boudjema | .................... 606/187 |
| 6,461,369 | B1 | | 10/2002 | Kim | |

* cited by examiner

*Primary Examiner*—Corrine McDermott
*Assistant Examiner*—Christopher Prone
(74) *Attorney, Agent, or Firm*—MacPherson Kwok Che & Heid LLP; David S. Park

(57) ABSTRACT

A hair implantation instrument herein employs a simple means for capturing a hair graft in a needle in a position for implantation into a scalp and an escapement mechanism for withdrawing the needle in a manner to leave the graft in the scalp. The needle is moved with respect to a rod which positions an implanted graft properly when the needle is withdrawn. The apparatus also defines a sheath over the needle for properly positioning a graft during a graft capture operation. The escapement mechanism is vacuum controlled in one embodiment and spring controlled in a second embodiment.

21 Claims, 6 Drawing Sheets

16, 18, 19, 20 Gauge Needle

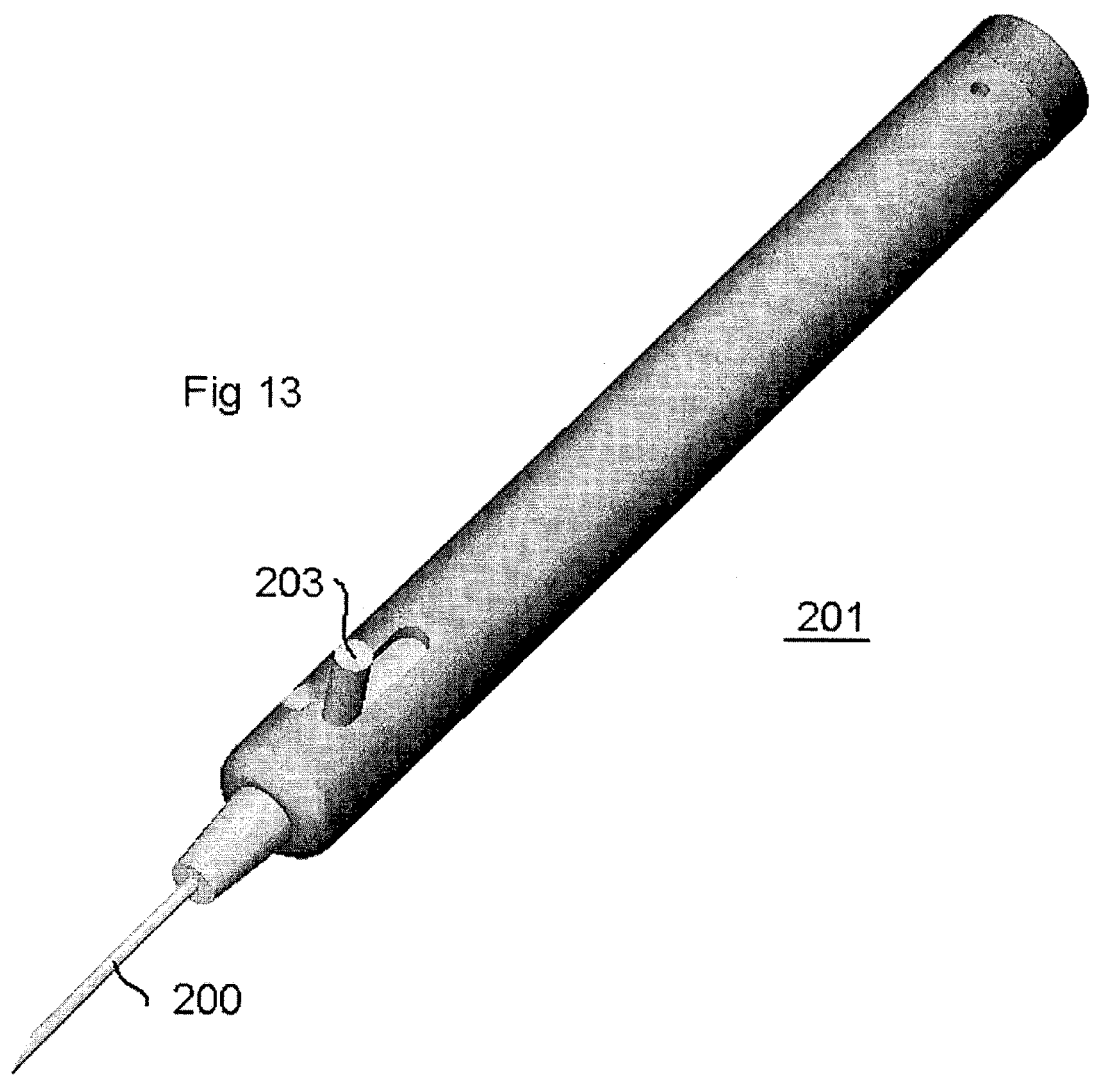

HAIR TRANSPLANT DEVICE

FIELD OF THE INVENTION

This invention relates to apparatus for transplanting hair grafts, and, more particularly to apparatus for implanting hair grafts primarily into a human scalp.

BACKGROUND OF THE INVENTION

The transplantation of hair grafts into a human scalp is well understood. The present state of the art calls for excising a hair-rich area of the scalp, dissecting the excised scalp segment to obtain individual grafts for implantation, creating an implantation site in a bald area of the scalp and implanting an individual graft into the prepared implantation site. It is also known that a preferred graft for implantation comprises a follicular unit which is the basic microscopic anatomy which contains 1–4 hairs bunched together.

Implantation instruments for use by a surgeon to implant hair grafts are well known. For example, U.S. Pat. No. 6,059,807, issued May 9, 2000 discloses a hair graft implantation instrument which includes a hollow needle which is moved within a sheath between first and second positions at which the needle extends beyond the sheath and at which the needle is retracted within the sheath. In operation, a vacuum is created within the needle when it is advanced to the first position to grasp a graft for implantation. The needle is inserted into a scalp as the vacuum is released. The needle is spring loaded to retract the needle to the second position.

The instrument disclosed in U.S. Pat. No. 6,059,807 is delicate to control requiring adjustment to position the needle tip to capture a graft. Moreover, implantation of a graft is difficult to achieve because of frequent removal of an implanted graft as the needle is withdrawn.

U.S. Pat. No. 6,461,369B1 issued Oct. 8, 2002 also discloses an instrument for hair graft implantation. The instrument disclosed in U.S. Pat. No. 6,461,369Bi comprises a needle with a slot for securing a hair to which a root is attached. The instrument also includes a sliding member which forms a sheath about the needle. The needle is inserted into the scalp and the surgeon depresses the sliding member towards the scalp as the needle is withdrawn, the sliding member operating to retain the graft in place. This instrument also requires a significant amount of training to coordinate the withdrawal of the needle and the manipulation of the sliding member.

BRIEF DESCRIPTION OF THE INVENTION

The present invention is based on the recognition that a hair graft implanting device has to perform not only to insert a hair graft into the scalp at a particular depth but also to extract the implanting needle in a manner which retains the hair graft in place. Such an extraction preferably occurs quickly in order to have a high success rate. But quick extraction of the needle also increases the risk of dislodging the graft.

In accordance with the principles of this invention, an implantation instrument includes a needle with an internal solid rod positioned along the axis of the needle and, importantly, is secured in a fixed position to the instrument housing. In operation, the needle is moved beyond the end of the rod the hair graft is loaded into the needle and the needle is inserted into a scalp. The needle is then quickly withdrawn via, for example, a spring loaded escapement mechanism. The fixed position rod is located to prevent dislodgment of the graft during the withdrawal of the needle.

Because of the fixed position of the rod and the movement and quick release of the needle, an operator need only insert the needle and activate an escapement trigger. The device requires no coordination of the needle withdrawal and the rod for preventing dislodgement of the graft during that withdrawal.

In one embodiment of this invention, an instrument, conveniently hand operated, serves to both grasp a hair graft from a scalp segment dissected from a human scalp and to implant the graft. The instrument comprises a cylindrical tube which includes first and second sealed chambers stacked in tandem along the central axis of the tube. Each chamber includes a piston which is movable forward and backward along the axis. Each piston is spring biased separately towards a distal end of the respective chamber. Each chamber also has a vacuum port or inlet positioned such that the creation of a vacuum operates to move the associated piston towards the proximal end of the tube, the end which is placed against a source of grafts or against the scalp, first to capture a graft and then to implant the graft.

The proximal end of the tube is open to permit the first piston to be advanced through the open proximal end of the tube into a source of hair grafts. The first piston has a hollow internal section and a section of reduced cross section which forms a sheath around the needle tip and which corresponds to the size of a hair graft. The first piston also includes an opening to permit an applied vacuum to be established also within the section of reduced cross section (sheath) to permit a suction there to allow the sheath to grasp a hair graft.

The tube also includes a rod in a fixed position along the axis of the tube and of a length to stop a hair graft from moving into the first piston further than an optimum position for implantation. The rod extends through each of the first and second pistons.

The second piston also includes an extension of reduced cross section. The extension extends along the axis of the tube into the first chamber and well into the first piston. The extension of the second piston ends in a needle.

The instrument is operated by applying a vacuum regimen first to capture a graft, drawing the graft into the sheath to a position determined by the rod. For this operation, the vacuum is applied to move both pistons to the proximal end of the tube. Next the vacuum for the first piston is turned off leaving the needle exposed beyond the proximal end of the tube. The vacuum for the second piston is still on.

Next, the vacuum for the second piston also is turned off, allowing the second piston (and the needle) to withdraw and the rod to act to properly maintain the captured graft in the scalp when the needle is withdrawn. So long as the instrument is abutted against an implantation site when the vacuum for the second piston is turned off, the graft is released as the graft is implanted.

Thus, in accordance with the principles of this invention, the sheath formed at the proximal end of the first piston draws in a hair graft when a vacuum is provided. The graft is guided into the tip of the needle while the needle is still retracted. The sheath then is withdrawn leaving the needle in position to implant the graft. The needle then is retracted about the rod which dislodges the graft leaving it in place when the needle is withdrawn.

In another embodiment, a graft is positioned within the needle from a source in a fluid medium.

The implementation for placing a graft within the needle need not be part of a single instrument. Instead, an instrument for implantation may mate with, for example, a vacuum operated graft capture device by insertion of the needle into the device in a sealed position for proper placement of a graft.

BRIEF DESCRIPTION OF THE DRAWINGS

FIG. 13 is a projection view of a third embodiment of this invention.

DETAILED DESCRIPTION OF AN ILLUSTRATIVE EMBODIMENT OF THIS INVENTION

Figure 1:
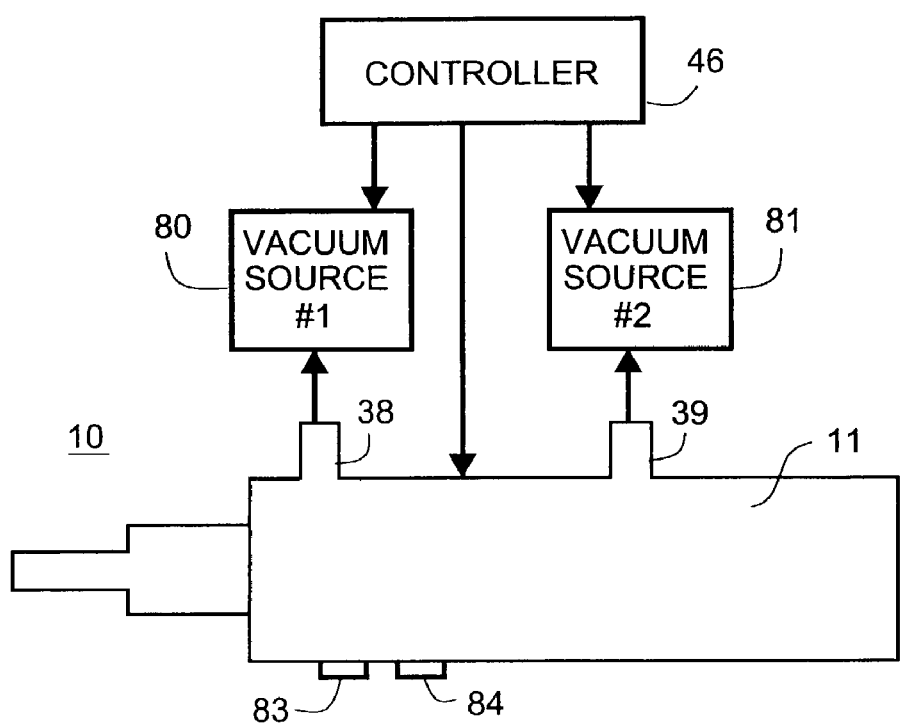
FIG. 1 is a schematic diagram of the system for hair graft capture and implantation in accordance with the principles of this invention.

FIG. 1 is a schematic representation of a system 10 for hair transplantation in accordance with the principles of this invention. The system includes an instrument 11 operative to capture a hair graft in a properly oriented and properly placed position for implantation into the human scalp.

Instrument 11, in one embodiment, is seven inches long and three-fourths of an inch in diameter and is normally held between the forefinger and the thumb. The index finger is left free to operate the instrument as will be more fully explained hereinafter.

The instrument is operative to capture a hair graft illustratively from a supply of grafts previously extracted from an excised portion of the scalp of the patent receiving the implantations.

Figure 2:
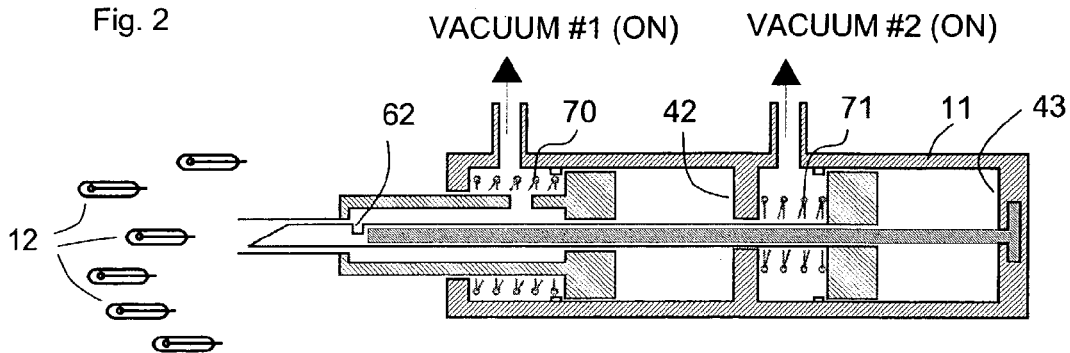
FIGS. 2, through 6 are schematic cross sections of a portion of the system of FIG. 1 showing the procedure for hair graft capture and implant in various stages of operation.

FIG. 2 represents individual hair grafts at 12. The instrument 11 of FIG. 1 is operated to capture a hair graft as an initial step in the implantation procedure.

Figure 3:
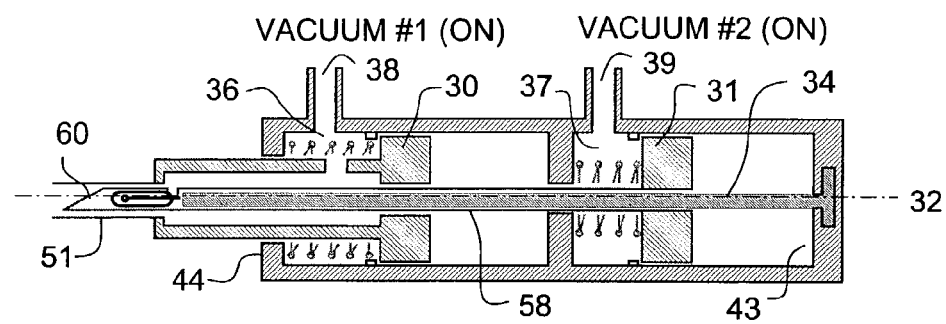
Figure 4:
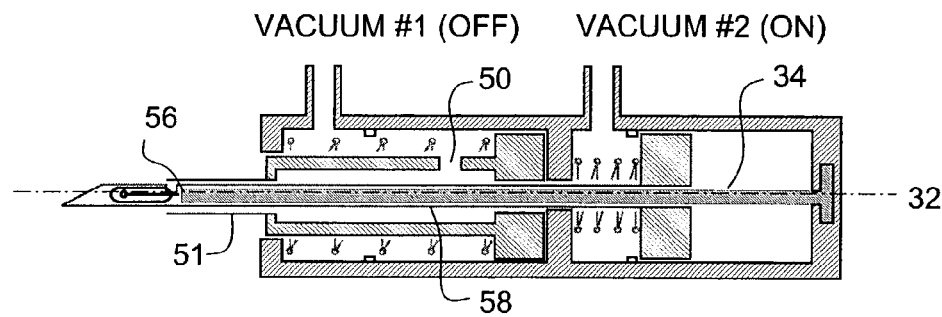
Figure 5:
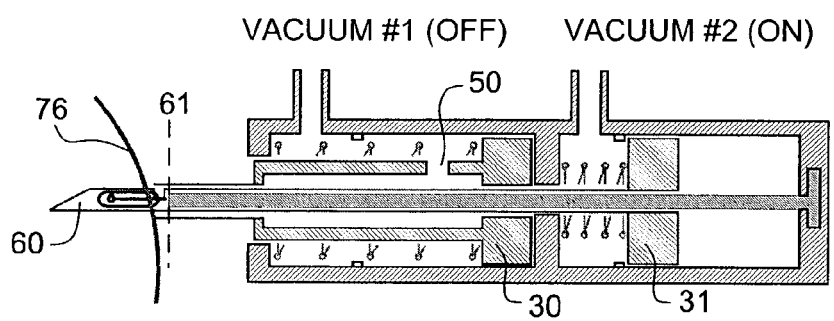

The operation of instrument 11 is described in connection with FIGS. 3–5. The instrument functions first to acquire a graft and then to insert the graft into the scalp. In the embodiment of FIGS. 3–5, a vacuum is used first to position a needle tip for insertion into the scalp and thereafter to capture the graft followed by an insertion of the needle into the scalp and finally a quick withdrawal of the needle in order to accomplish these functions With specific reference to FIG. 3, instrument 11 is shown in cross section. The instrument includes first and second pistons 30 and 31 having a common axis 32 coincident with the (conveniently central) axis of the instrument. Also, a rod 34 occupies a fixed position also aligned with the axis. The pistons and the rod, the successive positions of the pistons during operation, and the fixed position of the rod within the needle determine the capture, the proper positioning of the captured graft, the insertion of the graft and the needle withdrawal as is explained more fully hereafter.

Instrument 11 includes first and second chambers 36 and 37 and ports 38 and 39 respectively for creating vacuums in the chambers. Pistons 30 and 31 occupy chambers 36 and 37 respectively and are biased by springs normally towards the (distal) ends 42 and 43 of the chambers in the absence of vacuums.

Pistons 30 and 31 are operative to be moved towards the proximal end 44 of the instrument when vacuums are provided in the respective chambers as indicated in FIG. 3. The vacuums are provided selectively and in concert according to a regimen controlled, for example, by controller 46 of FIG. 1. The vacuums move the pistons illustratively along the central axis of the instrument.

Piston 30 is hollow so that a vacuum which is operative to move the piston towards the proximal end of the instrument also creates a vacuum within the piston through aperture 50 shown in FIG. 4. The proximal end 51 of piston 30 is of reduced diameter to a size which defines a sheath with dimensions to correspond to the dimensions of a needle. The suction in piston 30 causes a graft to be drawn into the sheath through aperture 62 to a position determined, for example, by the end 56 of rod 34. Rod 34 can be seen to extend from the proximal end of instrument 11 along the central axis of the instrument through both pistons 30 and 31 and is in a fixed position secured to the distal end of the instrument. The graft is now properly positioned with the graft follicular unit (root system) facing the open end of the instrument as shown in FIGS. 3, 4 and 5.

Piston 31 has an elongated portion 58 extending through piston 30 and terminating in a hollow needle configuration designated 60 in FIG. 5. Portion 58 can be seen to extend beyond end 56 of rod 34 when piston 31 is moved toward the open (proximal) end of the instrument.

Needle 60 has an aperture 62 which is within the (sealed) interior of Piston 30 as shown in FIG. 2. Thus, when a vacuum is present in chamber 36 it also is present within the needle 60 via aperture 62 and within the sheath of piston 30 via aperture 50. The presence of a vacuum (suction) within both the sheath and the needle insures that the proper capture and positioning of a graft occurs. Either of the rod end or the location of opening 62 may be used to properly locate a captured graft. Thus, the opening is located at about the rod tip to avoid any possible conflict in positioning the graft. But the rod end is operative alone to ensure that an implanted graft remains in place when the needle is withdrawn.

In operation, the vacuum for piston 30 is released for withdrawing the sheath and leaving the graft in position in needle 60 at the proximal end of rod 34. The advance of device 11 delivers the graft to the scalp of a patent through now exposed needle 60.

The graft is delivered preferably with a quick retraction of the needle so that the graft remains in the scalp when the needle is withdrawn. Further, the needle has to penetrate the scalp only a critical distance of approximately 5–6 mm. That distance is indicated by a line 61 which corresponds to the end 56 of rod 34. The retraction is accomplished by releasing the vacuum in chamber 37. This action allows spring 71 to return piston 31 and it's attached portion 58 (with needle 60) to distal end 43. At this point the tip of needle 60 is behind line 61.

The sequence of FIGS. 3–5 show the various positions of pistons 30 and 31 during operation with indications as to the status of the vacuums. When a vacuum is indicated to be off, the respective piston is biased towards the (distal) ends 42 and 43 of the respective chamber by springs 70 and 71 as shown in FIG. 6.

Figure 6:
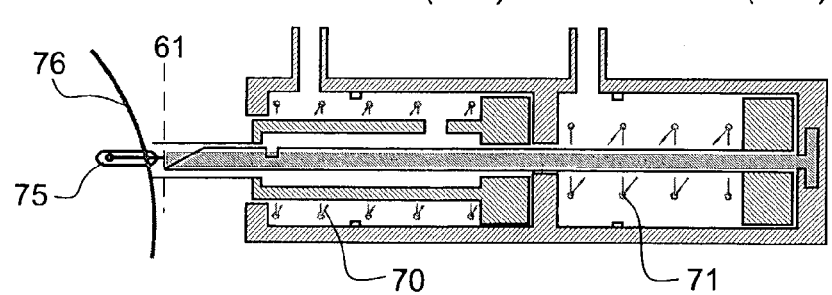

FIG. 6 represents the condition when both vacuums are off and a graft 75 is implanted in a scalp represented at 76 in FIG. 6.

Controller 46 of FIG. 1 is operative to activate pump 80, and pump 81 to create the requisite vacuum for chambers 36 and 37. The controller turns pump 80 on and off and turns pump 81 on and off to remove the vacuum selectively from chamber 36 and 37 when required as is discussed in connection with the flow diagram of the operation shown in FIG. 7. In practice, controller 46 is imbedded in instrument 11 and operated by "buttons" 83 and 84 of FIG. 1 by the index finger of the hair transplant specialist and indicated as individual vacuum sources No. 1 and No. 2 in FIG. 1.

Figure 7:
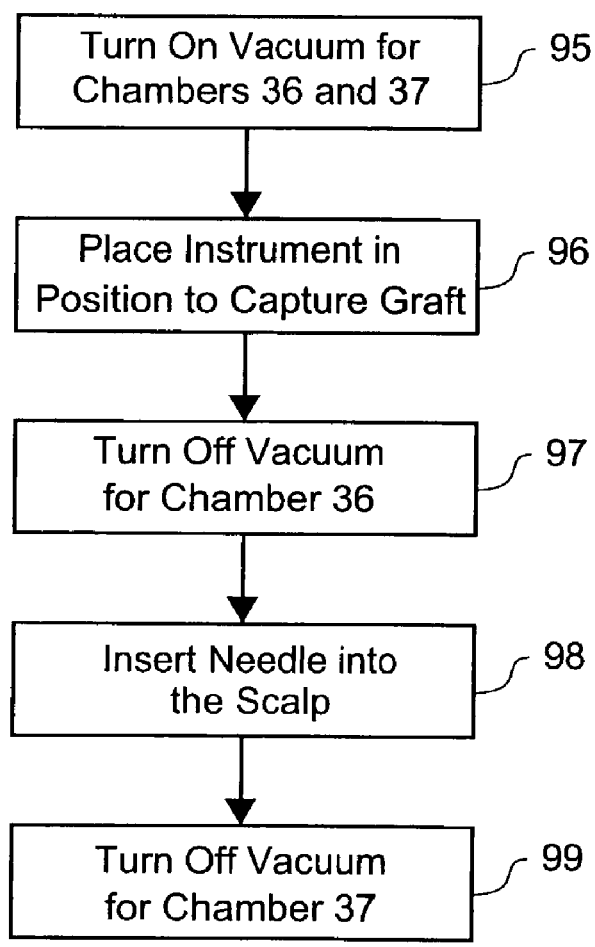
FIG. 7 is a flow diagram of the operation shown in FIGS. 2, 3, 4 and 5.

The status of the vacuums and the corresponding piston positions are indicated in the FIGS. The process is initiated by providing the vacuums for chambers 36 and 37 as indicated by block 95 of FIG. 7 and by the vacuum status legend in FIG. 3.

The second step in the process is to advance the instrument into a position to capture a graft 12 from a source of grafts as shown in FIG. 2. This step is indicated by block 96 of FIG. 7.

The next step is to turn off the vacuum in chamber 36 as indicated in block 97 of FIG. 7 to expose needle 60 as shown in FIG. 4.

The next step is to insert needle 60 into the scalp 76 as indicated by block 98 in FIG. 7 and in FIG. 5. The vacuum is then removed in chamber 37 as indicated by block 99 in FIG. 7 and by the vacuum status legend in FIG. 6 which results in the snap withdrawal of needle 60 leaving the graft in place in the scalp.

Figure 8:
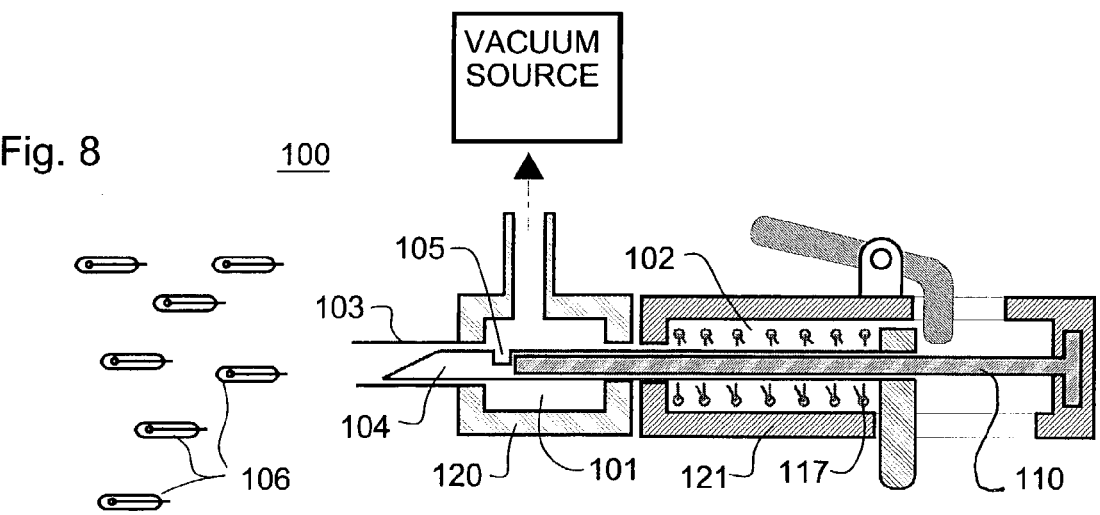
FIGS. 8–11 are schematic cross sections of the apparatus of a second embodiment of this invention representing the apparatus in various stages of operation.
Figure 9:
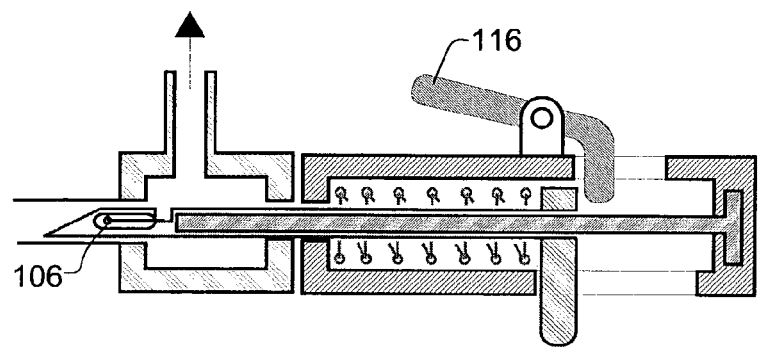

FIGS. 8–11 are schematic representations of another embodiment herein. The instrument 100 of FIGS. 8–11 also includes two chambers 101 and 102 as was the case with the embodiment of FIGS. 2–6. Chamber 101 includes a sheath 103; chamber 102 includes a needle 104. But in the second embodiment there are no pistons. The second embodiment may be considered to include two separate instruments acting as one instrument when they are joined together. Instead, a vacuum created in chamber 101 (and within sheath 103 and needle 104 through aperture 105) is operative to capture a graft 106 as shown in FIG. 9.

Figure 10:
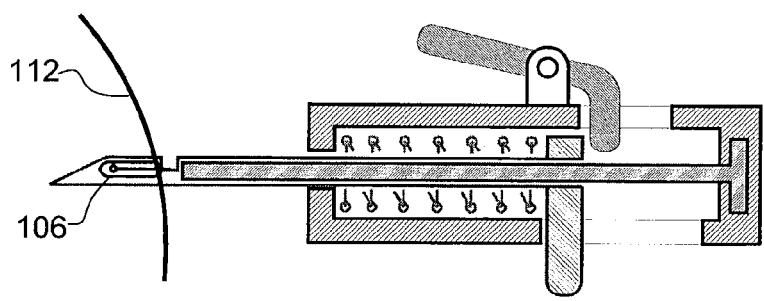
Figure 11:
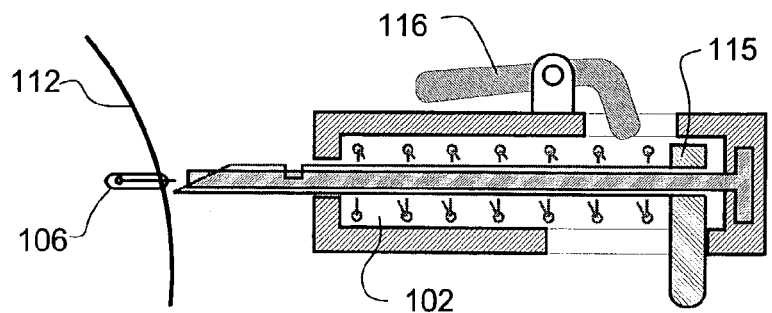

Instrument 100 also includes a rod 110 which remains in a fixed position within needle 104 with a proximal end positioned to properly maintain the position of an implanted graft (106) when needle 104 is withdrawn after implantation of a graft into the scalp 112 as shown in FIGS. 10 and 11. It is clear that instrument 100 is separated into two instruments 120 and 121. Once a graft is captured, instrument 121 then acts alone to become an implanter for the graft. The graft is loaded as shown in FIG. 9 by the provision of a vacuum within the sheath and the needle. FIG. 10 shows instrument 121 with a loaded graft, placed into the scalp 112. Instrument 121 may be removed from instrument 120 once a graft is captured as represented in FIG. 10.

Needle 104 is attached to element 115 (shown in FIG. 11) which limits the forward and backwards movement of needle 104 as is clear from FIGS. 8–10. The needle is movable backwards along the axis of the instrument when released by escapement latch 116 due to the bias provided by spring 117. The movement of the needle backwards leaves the apparatus in a position shown in FIG. 11 with the graft remaining in the scalp having been dislodged from the needle by rod 110.

Figure 12:
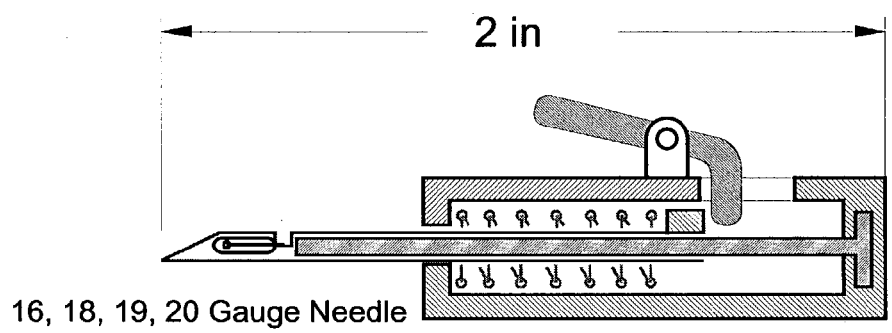
FIG. 12 is a full size cross section view of the apparatus of FIGS. 8–11.

FIG. 12 is a schematic cross section of a single shot hair transplanter of the type shown in FIGS. 8–11. The transplanter is shown in FIG. 11 and has a full size of two inches. The apparatus uses a 16, 18, 19 or 20 gauge needle.

In the embodiment of FIGS. 8–11, the portion of the apparatus 100 designated 121 is removable from the portion designated 120. Accordingly, portion 120 may be used as a community vacuum chamber with successive portions 121 being (quick) connected to portion 120 for capturing a graft as described above and then removed from portion 120 and positioned for graft implantation.

FIG. 13 is a projection view of a practical graft implanting instrument embodying the mechanism illustrated in FIGS. 10 and 11. The needle 200, in this embodiment, is again movable between first and second positions with respect to a coaxial rod which is in a fixed position with respect to the instrument housing. The instrument 201 includes a lever 203 which is moved downward and (as a latch) to the left as viewed, in FIG. 13, to advance the needle for inserting a graft previously loaded, into a scalp.

The advancement of the lever results in the lever being biased into a slot as shown in FIG. 13. Once the needle is inserted into the scalp, the lever is moved to disengage the slot. The needle is spring loaded in a manner explained in connection with FIGS. 10 and 11 and so is quickly withdrawn as lever 203 moves out of the slot back to a distal position. The rod (not shown in FIG. 13) prevents the graft from becoming dislodged.

Common to the various embodiments herein and most importantly is a rod which is in a fixed position within a hollow needle where the needle moves along a common axis with respect to the rod to a first position to implant a graft and to a second (withdrawn) position where the rod acts to retain a graft in place. Also, common to the various embodiments herein is a graft capture implementation where a graft is guided into position within a needle via a sheath, a vacuum being provided within the sheath (and simultaneously within the needle).

What has been described is considered merely illustrative of the invention. Those skilled in the art are clearly capable of producing variations thereof wherein the spirit and scope of the invention as encompassed by the following claims. It is clear, for example, that the presence of the rod herein properly retains an implanted graft in place and even permits slow needle withdrawal without a problem. Also, it is clear that graft capture may be accomplished manually.

What is claimed is:

1. Apparatus for implanting a hair graft into a scalp, said apparatus comprising a first chamber having an axis and a rod in a fixed position along said axis, said chamber including a hollow needle also aligned along said axis, said needle encompassing said rod and having a tip and a side opening therein spaced apart from said tip, said needle being movable along said axis between a first position at which said side opening is located near the end of said rod and a second position at which the needle tip is located at the end of said rod, the apparatus further including escapement means for withdrawing said needle to said second position, wherein said needle has a distal end attached to a spring loaded element movable in a manner to secure said needle in said second position.

2. Apparatus as in claim 1 also including means for communicating with said side opening for creating a vacuum within said needle.

3. Apparatus for implanting a hair graft into a scalp, said apparatus comprising a first chamber having an axis and a rod in a fixed position along said axis, said chamber including a hollow needle also aligned along said axis, said needle encompassing said rod and having a tip and a side opening therein spaced apart from said tip, said needle being movable along said axis between a first position at which said side opening is located near the end of said rod and a second position at which the needle tip is located at the end of said rod, the apparatus further including vacuum means for moving said needle to said first position, wherein said first chamber and said vacuum means are detachable from one another.

4. Apparatus for capturing a hair graft and implanting same in a scalp, said apparatus comprising a first tubular housing with an open proximal end and a central axis, said apparatus including first and second pistons movable controllably along said axis, said second piston including a tubular extension extending through said first piston and defining a needle extending beyond said open proximal end of said housing, said first piston defining a sheath for said needle and being movable to first and second positions to cover and expose said needle respectively, said second piston being movable to first and second positions for extending said needle to the exposed position and returning said needle to the covered position respectively, said apparatus further including a rod in a fixed position along said axis and having a proximal end in a position to expel any graft captured by said needle when said second piston is moved to the covered position.

5. Apparatus as in claim 4 wherein said housing includes first and second sealed chambers and said first and second pistons are positioned in said first and second chambers respectively, said apparatus further including first and second means for biasing said first and second pistons towards the distal end of said housing.

6. Apparatus as in claim 5 further including first and second vacuum means for moving said first and second pistons respectively along said axis towards said open proximal end of said housing.

7. Apparatus as in claim 6 also including third means for creating a vacuum within said first needle when said first piston is in a covered position.

8. Apparatus as in claim 7 wherein said housing includes vacuum inlet ports communicating with said first and second chambers for moving said first and second pistons controllably towards said open proximal end of said housing.

9. Apparatus as in claim 5 wherein said first and second means for biasing comprise first and second springs.

10. Apparatus as in claim 9 further comprising an opening for providing a vacuum within said needle when said first vacuum is operative to move said first piston to said first position.

11. Apparatus as in claim 10 also including user operated control means for controllably providing a first and second vacuum.

12. Apparatus for capturing a hair graft and implanting same in a scalp, said apparatus comprising a first tubular housing with an open proximal end and a central axis, said apparatus including first and second pistons movable controllably along said axis, said second piston including a tubular extension extending through said first piston and defining a needle extending beyond said open proximal end of said housing, said first piston being movable to first and second positions to cover and expose said needle respectively, said second piston being movable to first and second positions for extending said needle to an exposed position and returning said needle to a covered position respectively, said apparatus further including a rod in a fixed position along said axis and having a proximal end in a position to maintain in position any graft implanted by said needle when said second piston is moved to said second position.

13. Apparatus as in claim 12 wherein said housing includes first and second sealed chambers and said first and second pistons are positioned in said first and second chambers respectively, said apparatus including first and second means for moving said first and second pistons towards the distal end of said housing.

14. Apparatus as in claim 13 including first and second vacuum means for moving said first and second pistons along said axis towards said open proximal end of said housing.

15. Apparatus as in claim 14 also including third means for creating a vacuum within said first needle when said first piston is in said first position.

16. Apparatus as in claim 15 wherein said housing includes vacuum inlet ports communicating with said first and second chambers for moving said first and second pistons controllably towards said open proximal end of said housing.

17. Apparatus as in claim 16 further comprising first and second biasing means including first and second springs for moving said first and second pistons.

18. Apparatus including a hollow needle with a coaxial solid rod and a side opening spaced apart from a needle tip, said rod being in a fixed position with respect to said apparatus, means to move said needle between a first position with respect to said rod where the needle tip is at the end of the rod and a second position with respect to said rod where the needle tip and the side opening are beyond the rod, means for retaining a hair graft within said needle in the section between said first and second positions, and means for capturing including a sealable vacuum chamber, said chamber including a sheath-like extension and being adapted to receive a needle of a length to extend entirely through said chamber and into said sheath-like extension, wherein said vacuum chamber can be disengaged from said apparatus.

19. A chamber for containing a vacuum, said chamber having first and second opposing surfaces spaced apart a distance less than the length of a needle, said surfaces including first and second apertures respectively, said apertures being aligned along an axis and adapted to receive said needle in a manner to seal both of said apertures, said chamber also including a sheath extending along said axis externally from said second aperture, said chamber including a third surface perpendicular to said second surface, said third surface having a vacuum inlet port.

20. A chamber as in claim 19 in combination with a hollow needle extending into said first aperture along said axis and into said sheath, said needle having a side aperture.

21. A chamber as in claim 20 in further combination with means communicating with said vacuum inlet port for controllably producing a vacuum in said chamber and simultaneously in said needle.

* * * * *